(12) United States Patent
Badur (10) Patent No.: US 12,257,146 B2
(45) Date of Patent: Mar. 25, 2025

(54) INJECTOR ASSEMBLY FOR INSERTING AN INTRAOCULAR LENS

(71) Applicant: Carl Zeiss Meditec AG, Jena (DE)

(72) Inventor: Thorben Badur, Oberkochen (DE)

(73) Assignee: Carl Zeiss Meditec AG, Jena (DE)

( * ) Notice: Subject to any disclaimer, the term of this patent is extended or adjusted under 35 U.S.C. 154(b) by 5 days.

(21) Appl. No.: 17/875,142

(22) Filed: Jul. 27, 2022

(65) Prior Publication Data

US 2022/0362008 A1 Nov. 17, 2022

Related U.S. Application Data

(63) Continuation of application No. PCT/US2020/015193, filed on Jan. 27, 2020.

(51) Int. Cl.
*A61F 2/16* (2006.01)

(52) U.S. Cl.
CPC ............ *A61F 2/167* (2013.01); *A61F 2/1675* (2013.01); *A61F 2/1678* (2013.01)

(58) Field of Classification Search
CPC ...... A61F 2/167; A61F 2/1675; A61F 2/1678; A61F 2/1662; A61F 2/1667; A61F 2/1672
See application file for complete search history.

(56) References Cited

U.S. PATENT DOCUMENTS 4,464,174 A * 8/1984 Ennis .................... A61M 5/284
604/236
5,429,603 A * 7/1995 Morris .............. A61M 5/31596
604/87

(Continued)

FOREIGN PATENT DOCUMENTS

CN 201899603 U 7/2011
CN 102151194 A 8/2011
(Continued)

OTHER PUBLICATIONS

Search Report issued in Chinese Patent Application No. CN 202080094842.1, dated Dec. 28, 2022 and English language translation thereof.

(Continued)

*Primary Examiner* — Ashley L Fishback
*Assistant Examiner* — Chima U Igboko
(74) *Attorney, Agent, or Firm* — Ewers IP Law PLLC; Falk Ewers (57) ABSTRACT

An ophthalmosurgical injector includes a cannula, a barrel, an outer plunger mounted in the barrel and together with the barrel delimiting a barrel cavity arranged in the barrel, and into which an intraocular lens can be introduced, and an inner plunger mounted in the outer plunger and together with the outer plunger delimiting an outer plunger cavity arranged in the outer plunger and into which a liquid can be introduced. The injector is configured such that a first movement, executed by the inner plunger relative to the outer plunger such that the outer plunger cavity becomes smaller, causes the liquid to flow from the outer plunger cavity into the barrel cavity, and a second movement, executed by the outer plunger relative to the barrel such that the barrel cavity becomes smaller, causes the intraocular lens to be pressed out of the barrel cavity and into the cannula.

21 Claims, 5 Drawing Sheets

(56) References Cited

U.S. PATENT DOCUMENTS

| | | | | |
|---|---|---|---|---|
| 2005/0277894 A1* | 12/2005 | Westbye | ............... | A61M 5/326 |
| | | | | 604/198 |
| 2008/0097460 A1 | 4/2008 | Boukhny et al. | | |
| 2009/0292293 A1* | 11/2009 | Bogaert | ............... | A61F 2/1664 |
| | | | | 606/107 |
| 2010/0106160 A1 | 4/2010 | Tsai | | |

FOREIGN PATENT DOCUMENTS

| | | |
|---|---|---|
| EP | 1800623 A1 | 6/2007 |
| EP | 2060243 A1 | 5/2009 |
| JP | 2010063777 A | 3/2010 |
| JP | 2011200469 A | 10/2011 |
| JP | 2012010961 A | 1/2012 |

OTHER PUBLICATIONS

Office Action issued in Chinese Patent Application No. 202080094842. 1, dated Jan. 5, 2023, and English language translation thereof.
International Search Report dated Jan. 27, 2020 of international application PCT/US2020/015193 on which this application is based.

* cited by examiner

INJECTOR ASSEMBLY FOR INSERTING AN INTRAOCULAR LENS

CROSS REFERENCE TO RELATED APPLICATIONS

This application is a continuation application of international patent application PCT/US2020/015193, filed Jan. 27, 2020, designating the United States, and the entire content of this application is incorporated herein by reference.

TECHNICAL FIELD

The disclosure relates to an ophthalmosurgical injector for inserting an intraocular lens into the capsular bag of an eye.

BACKGROUND

When treating cataract of an eye, only a small incision is usually made in the cornea of the eye, said incision being large enough to allow a cannula to be inserted through the incision into the eye. After the incision has been made in the cornea, the lens of the eye is broken up by phacoemulsification and then aspirated from the capsular bag of the eye. An intraocular lens is then inserted into the eye. In doing this, the intraocular lens is folded, such that it fits through the cannula of an injector. The cannula is inserted into the capsular bag through the incision, and the folded intraocular lens is pushed by the injector through the cannula into the capsular bag, in which the intraocular lens unfolds and thus replaces the original lens.

The intraocular lens is pushed into the cannula, and out of the cannula into the capsular bag, with a plunger of the injector. In order to avoid damaging the intraocular lens when doing this, the intraocular lens is moved in the injector together with a lubricant and/or a physiological saline solution. In order to prepare the injector for the cataract treatment, several steps usually have to be taken by the surgical personnel performing the cataract treatment. These steps can, for example, involve equipping the injector with the intraocular lens, or with a liquid that has the lubricant and/or the physiological saline solution. The steps can also involve the manual removal of seals in order to bring the intraocular lens into contact with the liquid. Each of the steps may be susceptible to error, and the more steps that have to be performed the greater the probability of an error occurring. The occurrence of an error can lead to damage to the intraocular lens, which is a considerable drawback.

SUMMARY

It is an object of the disclosure to make available an injector that can be prepared for cataract treatment in a way that requires only a few steps.

The ophthalmosurgical injector according to an aspect of the disclosure has a cannula, a barrel, an outer plunger, which is mounted in the barrel in a longitudinally displaceable manner and together with the barrel delimits a barrel cavity which is arranged in the barrel and into which an intraocular lens can be introduced, and an inner plunger, which is mounted in the outer plunger in a longitudinally displaceable manner and together with the outer plunger delimits an outer plunger cavity which is arranged in the outer plunger and into which a liquid can be introduced, wherein the injector is designed such that a first movement, executed by the inner plunger relative to the outer plunger such that the outer plunger cavity becomes smaller, causes the liquid to flow from the outer plunger cavity into the barrel cavity via an opening arranged in the outer plunger, and a second movement, executed by the outer plunger relative to the barrel such that the barrel cavity becomes smaller, causes the intraocular lens to be pressed out of the barrel cavity and into the cannula.

The injector can be supplied together with the intraocular lens arranged in the barrel cavity and together with the liquid arranged in the outer plunger cavity. In cataract treatment, it is in this case simply necessary, before insertion of the intraocular lens, to perform the first movement in order thereby to allow the liquid to flow into the barrel cavity and thus bring the intraocular lens into contact with the liquid. For example, it is not necessary to manually remove a conventional seal in order to bring the intraocular lens into contact with the liquid. When the injector is supplied together with the intraocular lens arranged in the barrel cavity and together with the liquid arranged in the outer plunger cavity, it is possible for the injector, the intraocular lens and the liquid to be sterilized in a single method step, which simplifies the production of the injector.

For example, the injector can be sterilized by gamma radiation. When the injector is supplied without the intraocular lens and/or without the liquid and therefore the intraocular lens and/or the liquid have to be introduced into the injector prior to the cataract treatment, the number of steps can be reduced by comparison with a conventional injector, this being achieved by dispensing with the manual removal of the conventional seal or with the usually manual application of a lubricant into the barrel cavity. It is moreover possible, during the first movement, that an air bubble arranged in the barrel cavity can be pressed completely out of the barrel cavity via the cannula. In this way, the intraocular lens can be brought fully into contact with the liquid, which reduces the risk of damaging the intraocular lens. Since the liquid is arranged in the outer plunger, the injector can moreover be configured in a particularly compact format. It is additionally possible to operate the injector with just one hand.

It is typical that the outer plunger has a seal which seals off the outer plunger cavity from the barrel cavity and which is designed to be caused to burst with the first movement. The liquid penetrates the seal as the latter bursts. By providing the seal, it is advantageously possible, before using the injector, to keep the liquid far from the barrel cavity and to fill the latter with the liquid only during the cataract treatment. It is thereby possible that the barrel has, in the region of the barrel cavity, a coating which makes it easier for the intraocular lens to slide in the injector. It would be disadvantageous for the coating to be in contact with the liquid over a long period of time, because the coating comes loose over time upon contact with the liquid. Since the seal is caused to burst with the first movement, it is also not necessary to remove the seal by hand.

The outer plunger typically has a nozzle via which the liquid flows from the outer plunger cavity into the barrel cavity. A nozzle is understood as any cross-sectional narrowing that the liquid experiences when the liquid flows from the outer plunger cavity into the barrel cavity during the first movement. The liquid flows from the opening through the cross-sectional narrowing at a higher speed than the speed at which the first movement is executed. By virtue of the higher speed, the intraocular lens at the start of the first movement is wetted more uniformly with the liquid than would be the case if the nozzle were not provided.

It is typical that the outer plunger has, at its end delimiting the barrel cavity, a cushion which is designed to contact the intraocular lens during the second movement. Since the cushion is softer than the rest of the outer plunger, it is unlikely that the intraocular lens will be damaged by the outer plunger during the second movement. It is particularly typical that the barrel cavity has a narrowed part at its end facing away from the outer plunger, and the cushion is designed such that the cushion, when moved into the narrowed part, is deformed such that the opening is reduced in size or closed. It is thereby possible to reduce or avoid a return flow of the liquid from the barrel cavity into the outer plunger cavity via the opening during the second movement. The narrowed part is also designed such that the intraocular lens is folded here, as a result of which it can pass into the cannula. Since the cushion is deformed during the movement, the cushion can moreover push the intraocular lens into the cannula and then out of the cannula.

A rigid channel is typically arranged in the cushion, which rigid channel allows the liquid to flow from the barrel cavity in a direction away from the cannula. The rigid channel is designed not to be deformed during the movement of the cushion into the narrowed part. In this way, the amount of the liquid that flows from the injector into the capsular bag during the cataract treatment can be reduced. The rigid channel can be arranged such that the liquid flows back into the outer plunger cavity. Alternatively, the injector can have a collection container spatially separate from the outer plunger cavity and the barrel cavity, and the rigid channel can be arranged such that the liquid flows into the collection container. It is moreover conceivable that, in addition to the rigid channel, a flexible channel is arranged in the cushion, which flexible channel is designed to be deformed during the movement of the cushion into the narrowed part, such that the opening is reduced in size or closed.

The outer plunger typically has a channel, which is arranged directly upstream from the opening and via which the liquid flows to the opening during the first movement, and a channel wall, which delimits the channel and which is arranged at a distance from the barrel. This is especially relevant if the narrowed part is provided, because the channel can extend together with the channel wall into the narrowed part, which makes it easier to push the intraocular lens into the cannula. The terms "upstream" and "downstream" relate here to the flow of the liquid when the liquid flows from the outer plunger cavity into the barrel cavity during the first movement.

The injector typically has a locking device which has a locked state, in which the second movement is blocked and the first movement is permitted, and an unlocked state, in which the second movement is no longer blocked. With the locking device, it is advantageously possible to perform and complete the first movement only in the locked state, as a result of which the barrel cavity can be filled with the liquid, and then to bring the locking device to the unlocked state. In this way, the outer plunger can be moved only when there is enough of the liquid in the barrel cavity to reduce the danger of damage to the intraocular lens.

It is typical that the locking device has a pin, which is mounted on the barrel, and the outer plunger has a first outer plunger wall portion, in which an outer plunger cutout is formed, wherein, in the locked state, the pin is arranged in the outer plunger cutout and, in the unlocked state, the pin is arranged outside the outer plunger cutout. When the pin is arranged in the outer plunger cutout, the first outer plunger wall portion, during its movement relative to the barrel, abuts the pin, as a result of which the second movement is blocked. By contrast, when the pin is arranged outside the outer plunger cutout, the outer plunger can execute the second movement unimpeded. It is particularly typical that, in the locked state, the pin is mounted fixedly on the barrel and protrudes inward from the barrel, and the barrel has a predetermined breaking point, the deformation of which permits removal of the pin from the outer plunger cutout. Deformation is intended to signify both a bending of the predetermined breaking point, as a result of which the pin can be bent out from the outer plunger cutout but still remains secured to the rest of the barrel, and also a rupture of the predetermined breaking point, as a result of which the pin is completely separable from the rest of the barrel. Alternatively, it is particularly typical that the barrel has a barrel through-hole through which, in the locked state, the pin extends into the outer plunger cutout. It is possible here to pull the pin out of the outer plunger cutout or alternatively to press it out.

The barrel typically has a cutout with a first region and a second region, and the locking device typically has a switching mechanism, which is arranged in the barrel and is designed to abut the outer plunger in order thereby to block the second movement, and has a projection, which engages in the cutout, wherein, in the locked state, the projection engages in the first region, from where the projection can be brought into the second region by a rotation of the switching mechanism, as a result of which the locking device reaches the unlocked state. It is conceivable here that the switching mechanism is designed such that the rotation of the switching mechanism is effected with the switching mechanism being rotated by hand. This can be achieved, for example, by the cutout being a through-hole and by the projection protruding outward from the barrel. Moreover, it is conceivable that the locking device has a pretensioning means, which is supported on the barrel and pretensions the switching mechanism in a direction away from the cannula. By way of example, the pretensioning means can be a compression spring. It is particularly typical that the end of the first region facing toward the cannula is arranged farther away from the cannula than the end of the second region facing toward the cannula. The injector is particularly typically designed to convert part of the second movement into the rotation of the switching mechanism. In this way, it is advantageously unnecessary to rotate the switching mechanism by hand, and instead the rotation of the switching mechanism is effected by pressing on the inner plunger or by the restoring force of a pretensioning means.

The injector is typically designed such that the first movement is effected with a translation movement of the inner plunger, and the second movement is effected with a screwing movement of the outer plunger. For this purpose, the barrel can have an internal thread and the outer plunger can have an external thread, wherein the internal thread and the external thread are in engagement with each other. To avoid the danger of damage to the intraocular lens during the second movement, it is merely necessary to first press the inner plunger in the direction toward the cannula, until there is enough of the liquid present in the barrel cavity, and then to rotate the outer plunger. Alternatively, it is conceivable that the injector is designed such that the first movement is effected with a translation movement of the inner plunger, and the second movement is effected with a translation movement of the outer plunger. It is conceivable here that the movement of the inner plunger has less resistance than that of the outer plunger, as a result of which the two movements are executed in this sequence. It is moreover conceivable that the first movement is effected with a translation movement of the inner plunger, and the second rotation movement of the outer plunger is effected by a conversion of the translation movement of the inner plunger, for example by a rotatably mounted plunger endpiece.

It is typical that the injector has a heating element, which is designed to heat the outer plunger cavity. By heating the liquid located in the outer plunger cavity, the viscosity of the liquid can be lowered, as a result of which the flow resistance of the liquid during the first movement and/or during the second movement is reduced. The heating element typically has a latent heat store. The latent heat store is typically a supersaturated solution, which is designed to emit heat through crystallization of the supersaturated solution. It is particularly typical that the inner plunger has a crystallization protuberance which is designed, during the first movement, to contact the supersaturated solution and thereby trigger the crystallization. The crystallization protuberance can be a seed crystal, for example. As an alternative to the latent heat store, the heating element can have an electric heater, or the heating element is designed to release heat with a chemical reaction, in particular an oxidation.

The injector is typically designed to receive a cartridge in which the liquid is arranged, as a result of which the liquid can be introduced into the outer plunger cavity.

It is typical that the injector has the intraocular lens, and the intraocular lens is arranged in the barrel cavity. Alternatively to the intraocular lens, the injector can also have another ophthalmic device, which is arranged in the barrel cavity.

It is typical that the injector has the liquid, and the liquid is arranged in the outer plunger cavity. The liquid typically has a lubricant and/or a physiological saline solution or consists of the lubricant and/or the physiological saline solution. The lubricant can be an ophthalmic viscoelastic device (OVD).

BRIEF DESCRIPTION OF THE DRAWINGS

The disclosure will now be described with reference to the drawings wherein.

DESCRIPTION OF EXEMPLARY EMBODIMENTS

Figure 1:
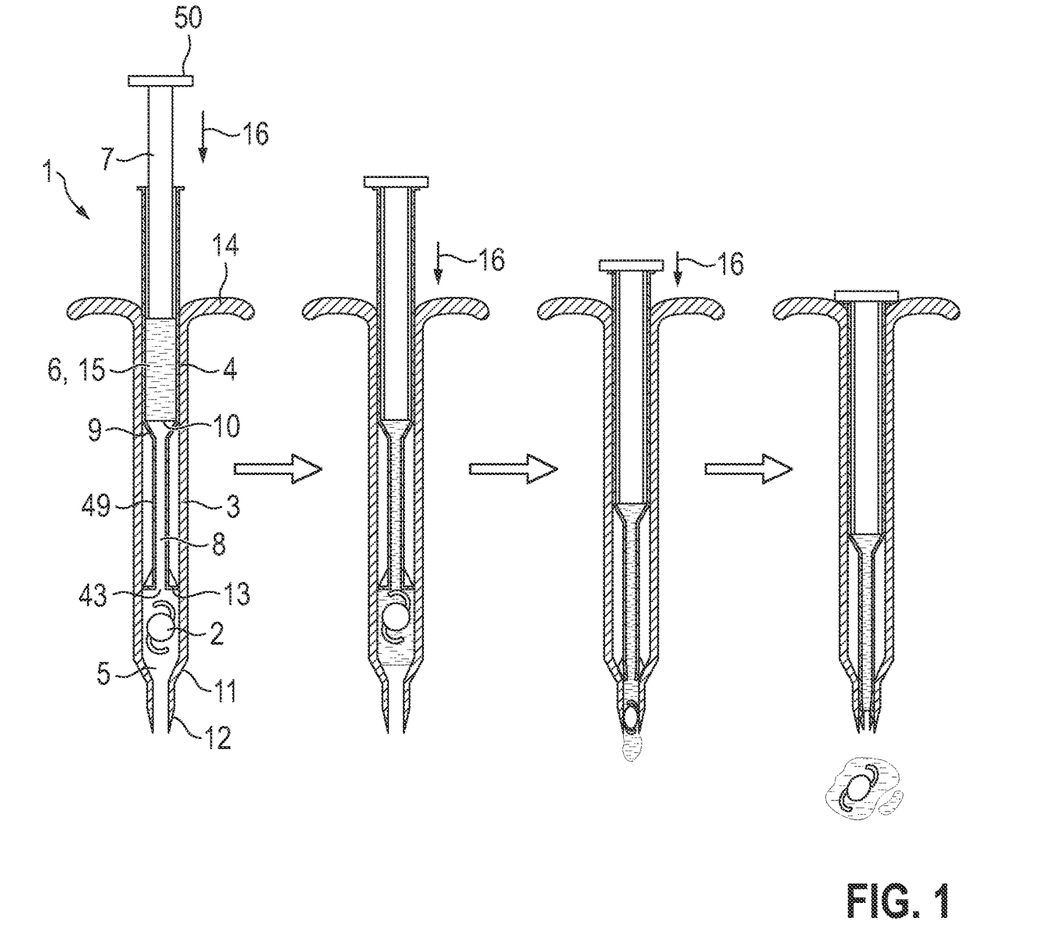
FIG. 1 shows a first exemplary embodiment of the injector.

As will be seen from FIG. 1, an ophthalmosurgical injector 1 according to all of the exemplary embodiments has a cannula 12, a barrel 3, an outer plunger 4 and an inner plunger 7. The outer plunger 4 is mounted in the barrel 3 in a longitudinally displaceable manner and together with the barrel 3 delimits a barrel cavity 5 arranged in the barrel 3. Moreover, the outer plunger 4 has an opening 43 arranged in the outer plunger 4. An intraocular lens 2 can be introduced into the barrel cavity 5. The inner plunger 7 is mounted in the outer plunger 4 in a longitudinally displaceable manner and together with the outer plunger 4 delimits an outer plunger cavity 6 arranged in the outer plunger 4. A liquid 15 can be introduced into the outer plunger cavity 6. The injector 1 is designed such that a first movement, executed by the inner plunger 7 relative to the outer plunger 4 such that the outer plunger cavity 6 becomes smaller, causes the liquid 15 to flow from the outer plunger cavity 6 into the barrel cavity 5 via the opening 43 arranged in the outer plunger 4. Moreover, the injector 1 is designed such that a second movement, executed by the outer plunger 4 relative to the barrel 3 such that the barrel cavity 5 becomes smaller, causes the intraocular lens 2 to be pressed out of the barrel cavity 5 and into the cannula 12.

In all the exemplary embodiments, the injector 1 can have the intraocular lens 2, and the intraocular lens 2 can be arranged in the barrel cavity 5. Moreover, the injector 1 can have the liquid 15, and the liquid 15 can be arranged in the outer plunger cavity 6. The liquid 15 can have a lubricant and/or a physiological saline solution or can consist of the lubricant and/or the physiological saline solution.

Figure 7:
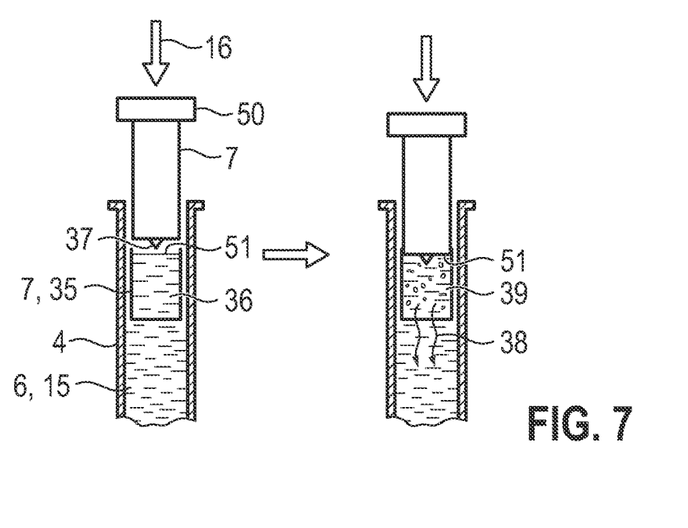
FIG. 7 illustrates the use of a latent heat store in the injector.

In FIGS. 1 and 7, an arrow shows by way of example an insertion direction 16 in which the inner plunger 7 is to be pressed in order to bring about the first movement and optionally also the second movement. The inner plunger 7 can be pressed by hand, wherein an injector assembly is also conceivable which has the injector 1 and a motor designed to drive the inner plunger 7.

FIG. 1 shows that the injector 1 can have a handle 14 secured on the barrel 3.

Figure 6:
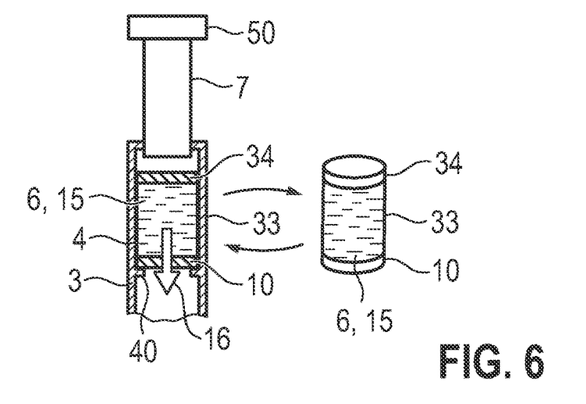
FIG. 6 illustrates the use of a cartridge in the injector.

FIGS. 1 and 6 show that the outer plunger 4 can have a seal 10 which seals off the outer plunger cavity 6 from the barrel cavity 5 and which is designed to be caused to burst with the first movement. The seal 10 can for this purpose be arranged in the opening 43 or upstream from the opening 43. The terms "upstream" and "downstream" relate here to the flow of the liquid 15 when the liquid 15 flows from the outer plunger cavity 6 into the barrel cavity 5 during the first movement.

As can be seen from FIG. 1, the outer plunger 4 can have, at its end delimiting the barrel cavity 5, a cushion 13 which is designed to contact the intraocular lens 2 during the second movement, wherein the cushion 13 is softer than the rest of the outer plunger 4. Moreover, the barrel cavity 5 can have a narrowed part 11 at its end facing away from the outer plunger 4, and the cushion 13 can be designed such that the cushion 13, when moved into the narrowed part 11, is deformed such that the opening 43 is reduced in size or closed.

FIGS. 1 to 5 show that the outer plunger 4 can have a channel 8, which is arranged directly upstream from the opening 43 and via which the liquid 15 flows to the opening 43 during the first movement, and a channel wall 49, which delimits the channel 8 and which is arranged at a distance from the barrel 3.

FIG. 1 shows the injector 1 by way of example at four different time points, wherein the injector 1 is shown at the earliest time point on the left, and the time progresses toward the right. At the first time point, the seal 10 is intact, and the outer plunger cavity 6 is filled with the liquid 15. The inner plunger 7 is then moved in the direction toward the cannula 12, as a result of which the first movement is executed. In this way, the seal 10 bursts and the liquid 15 flows from the outer plunger cavity 6 into the barrel cavity 5 via the opening 43. At the second time point, the first movement is concluded. Here, the end of the inner plunger 7 facing toward the cannula 12 abuts the outer plunger 4. Alternatively or additionally, it is conceivable that the inner plunger 7 has a thickened part 50 which protrudes outward from the rest of the inner plunger 7, perpendicularly to the direction of the first movement, and abuts the outer plunger 4 at the second time point. By further movement of the inner plunger 7 toward the cannula 12, the inner plunger 7 and the outer plunger 4 now move together, as a result of which the second movement is executed. During the second movement, the cushion 13 contacts the intraocular lens 2, and the intraocular lens 2, together with the liquid 15, is moved from the outer plunger 4 to the cannula 12. The intraocular lens 2 is pushed into the narrowed part 11, where it is folded. Thereafter, the intraocular lens 2 passes into the cannula 12, where it is located at the third time point. The cushion 13 is located in the narrowed part 11, and it can be seen that the cushion 13 has deformed when entering the narrowed part 11. The intraocular lens 2 is then pushed out of the cannula 12. This is shown at the fourth time point, where it can be seen that the cushion 13 has deformed further and is located in the cannula 12. It is also conceivable that part of the channel 8 is arranged in the cannula 12.

FIGS. 1 to 5 show that the outer plunger 4 can have a nozzle 9 via which the liquid 15 flows from the outer plunger cavity 6 into the barrel cavity 5. The nozzle 9 is understood as any cross-sectional narrowing that the liquid 15 experiences when the liquid 15 flows from the outer plunger cavity 6 into the barrel cavity 5 during the first movement. The liquid 15 flows from the opening 43 through the cross-sectional narrowing at a higher speed than the speed at which the first movement is executed. In the case where the seal 10 is provided, the seal 10 can be provided, as shown in FIG. 1, upstream from the nozzle 9. Alternatively, it is conceivable that the seal 10 is provided downstream from the nozzle 9. This has the effect that, during the first movement, the pressure at the seal 10 is higher than if the seal 10 were arranged upstream from the nozzle 9. As a result of the higher pressure, the seal 10 bursts more easily during the first movement. It is also possible to arrange the seal 10 in the nozzle 9.

Figure 2:
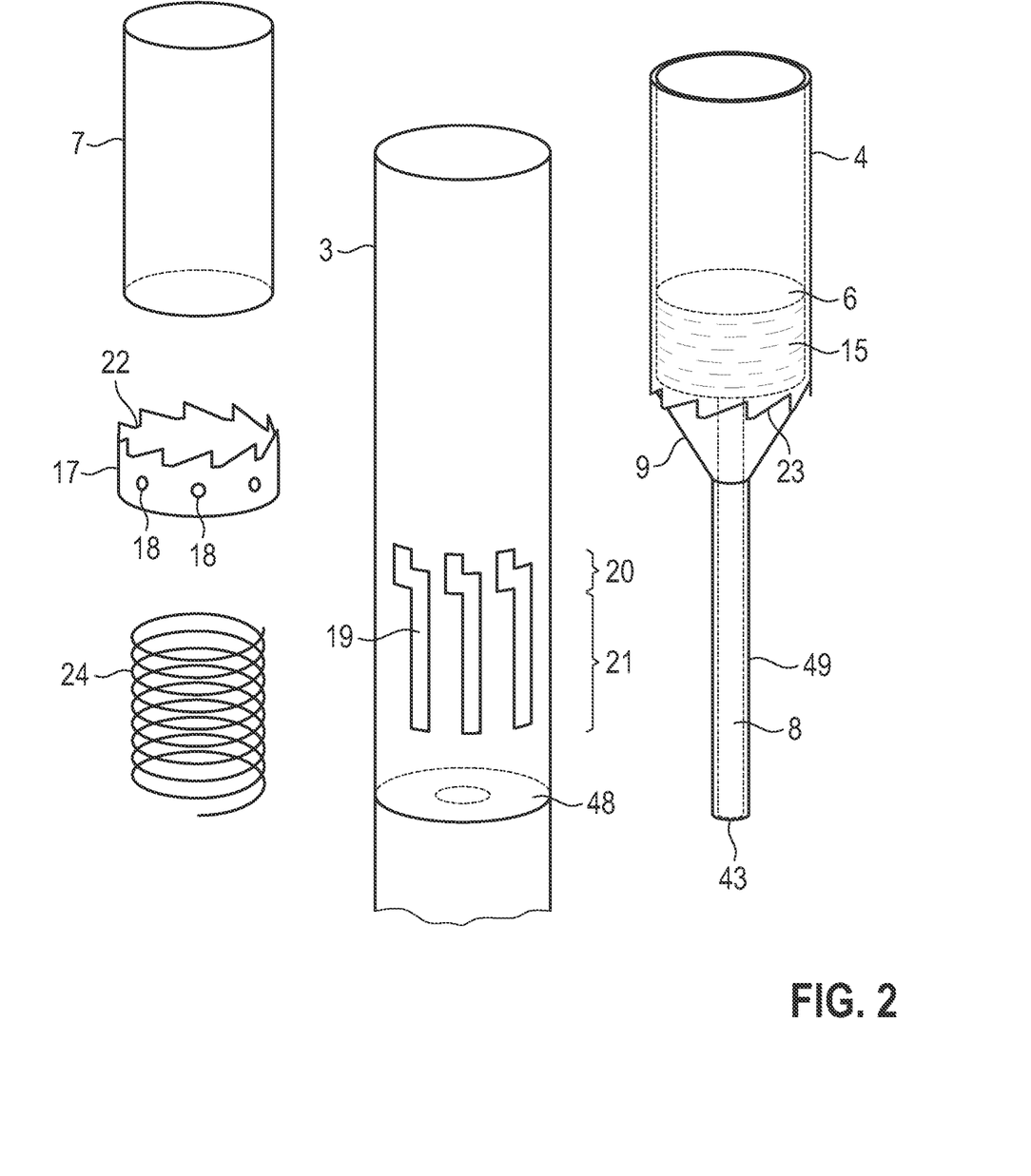
FIGS. 2 and 3 show a second exemplary embodiment of the injector.
Figure 3:
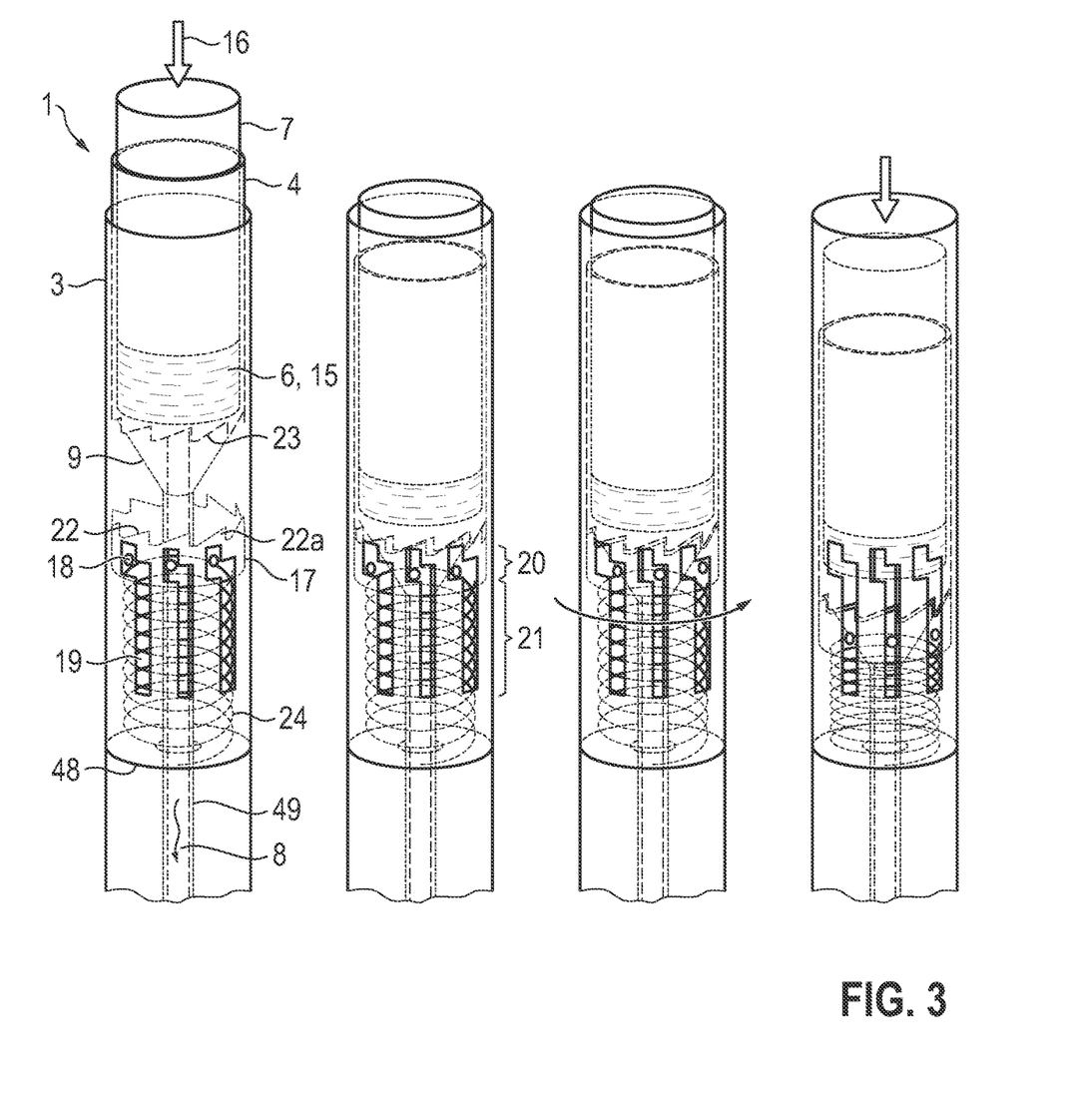
Figure 4:
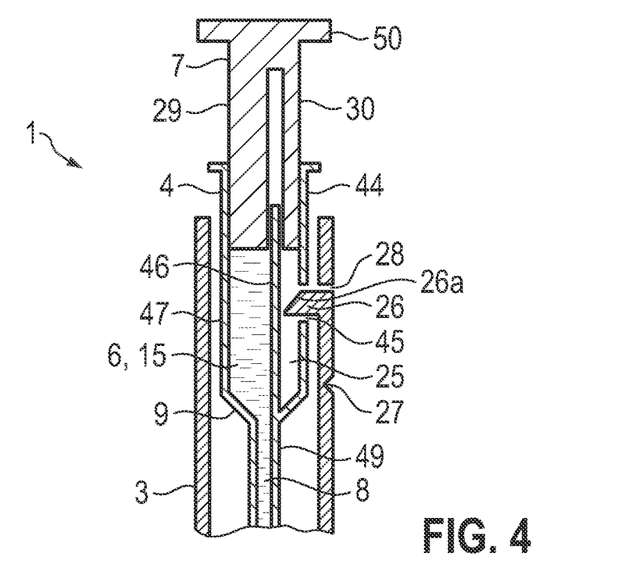
FIG. 4 shows a third exemplary embodiment of the injector.

As is shown in FIGS. 2 to 5, the injector 1 can have a locking device which has a locked state, in which the second movement is blocked and the first movement is permitted, and an unlocked state, in which the second movement is no longer blocked. FIGS. 2 and 3 show an exemplary embodiment of the locking device, and FIG. 4 shows another exemplary embodiment of the locking device, wherein FIG. 2 shows individual parts of the injector 1 in a dismantled state, and FIG. 3 shows the individual parts from FIG. 2 in an assembled state.

According to FIGS. 2 and 3, the barrel 3 can have a cutout 19, and the locking device can have a switching mechanism 17. The switching mechanism 17 is arranged in the barrel 3 and is designed to abut the outer plunger 4 in order thereby to block the second movement. Moreover, the switching mechanism 17 has a projection 18 which engages in the cutout 19. The cutout 19 has a first region 20 and a second region 21, wherein the end of the first region 20 facing toward the cannula 12 is arranged farther away from the cannula 12 than the end of the second region 21 facing toward the cannula 12. In the locked state, the projection 18 engages in the first region 20. From the first region 20, the projection 18 can be brought into the second region 21 by a rotation of the switching mechanism 17, as a result of which the locking device reaches the unlocked state. Moreover, the locking device can have a pretensioning means 24, in particular a compression spring, which is supported on the barrel 3 and pretensions the switching mechanism 17 in a direction away from the cannula 12. For this purpose, the barrel 3 can have a spring support 48, which protrudes inward. Alternatively, it is conceivable that the pretensioning means 24 is supported at a region of the barrel 3, wherein the region is an end of the barrel cavity 5 lying downstream. FIGS. 2 and 3 moreover show that the end of the first region 20 facing away from the cannula 12 can be arranged farther away from the cannula 12 than the end of the second region 21 facing away from the cannula 12. Together with the pretensioning means 24, it can thus be ensured that the projection 18 does not accidentally move from the first region 20 into the second region 21. As can be seen from FIGS. 2 and 3, it is also conceivable that there are several cutouts 19, and for each of the cutouts 19 one of the projections 18 is provided, wherein each of the projections 18 engages in another of the cutouts 19.

FIGS. 2 and 3 moreover show that the injector 1 can be designed to convert part of the second movement into the rotation of the switching mechanism 17. For this purpose, the switching mechanism 17 can have a contact surface 22, which is arranged facing toward the outer plunger 4, and the outer plunger 4 can have an outer plunger projection 23, which is arranged facing toward the contact surface 22. The switching mechanism 17 moreover has a switching mechanism projection 22a, which protrudes from the contact surface 22 and is arranged facing toward the outer plunger projection 23. If the farthest protruding point of the outer plunger projection 23 projects in the direction of the second movement toward the switching mechanism 17, the resulting projection point is then located on a flank of the switching mechanism projection 22a. The outer plunger 4 is mounted in such a way that it cannot rotate in the barrel 3. It is also conceivable that several of the outer plunger projections 23 are provided, and a respective switching mechanism projection 22a is provided for each of the outer plunger projections 23.

FIG. 3 now illustrates the function by which, with the contact surface 22, the switching mechanism projection 22a and the outer plunger projection 23, part of the second movement can be converted into the rotation of the switching mechanism 17. FIG. 3 shows the injector 1 at four different times, wherein the injector 1 is shown at the earliest time point on the left, and the time progresses toward the right. At the first time point, the outer plunger 4 is spaced apart from the switching mechanism 17. The outer plunger 4 is then moved toward the switching mechanism 17, until the farthest protruding point of the outer plunger projection 23 abuts the projection point. By further movement of the outer plunger 4, the switching mechanism 17 is moved in the direction toward the cannula 12 until the projection 18, at the second time point, abuts the end of the first region 20 facing toward the cannula 12. By further pressing of the outer plunger 4, the farthest protruding point of the outer plunger projection 23 slides along the flank of the switching mechanism projection 22a in the direction toward the contact surface 22. Since the outer plunger 4 is mounted such that it cannot rotate in the barrel 3, the switching mechanism 17 is thus forced to perform the rotation, as a result of which the projection 18 is brought into the second region 21 at the third time point. The outer plunger 4 can then further perform the second movement, which is shown at the fourth time point. During a use of the injector 1, the outer plunger 4 can be pressed with little force up until the second time point. Starting from the second time point, the pretensioning force of the pretensioning means 24 becomes noticeable, and more force has to be applied to move the outer plunger 4 further, in order thereby to bring the locking device to the unlocked state. It is also conceivable that the outer plunger 4, at a constant force, cannot be moved in one movement beyond the second time point. This is achieved by the projection 18 meshing with the end of the first region 20 directed toward the cannula 12. Only after the outer plunger 4 has relaxed does the switching mechanism 17 experience an automatic rotation movement, shown at the third time point. This movement of the switching mechanism 17 is driven by the counterforce of the pretensioning means 24, it being conceivable that the amount of stored energy can be adjusted by a variation of the pretensioning means 24 and by the length of the first region 20. After the rotation, the locking device is located in the unlocked state, and the second movement can be executed. By the incorporation of the switching mechanism 17, which permits the second movement only after relaxation of the inner plunger 7, i.e., priming of the injector 1, an exact transition point between the preparation phase (mostly performed by the physician's assistant) and the lens injection (performed by the physician) can be defined and ensured.

According to FIG. 4, the locking device can have a pin 26, which is mounted on the barrel 3, and the outer plunger 4 can have a first outer plunger wall portion 44, in which an outer plunger cutout 45 is formed, wherein, in the locked state, the pin 26 is arranged in the outer plunger cutout 45 and, in the unlocked state, the pin 26 is arranged outside the outer plunger cutout 45. For this purpose, the outer plunger 4 can have a further outer plunger cavity 25, which is spatially separate from the outer plunger cavity 6 and into which the pin 26 extends in the locked state. The liquid 15 is not intended to be introduced into the further outer plunger cavity 25. A second outer plunger wall portion 45 delimits both the outer plunger cavity 6 and the further outer plunger cavity 25, and a third outer plunger wall portion 47 delimits only the outer plunger cavity 6. Moreover, the inner plunger 7 can have a first inner plunger portion 29, which is mounted on the second outer plunger wall portion 46 and on the third outer plunger wall portion 47, and a second inner plunger portion 30, which is mounted on the second outer plunger wall portion 46 and on the first outer plunger wall portion 44.

FIG. 4 shows that, in the locked state, the pin 26 can be mounted fixedly on the barrel 3 and protrudes inward from the barrel 3, and the barrel 3 can have a predetermined breaking point 27, the deformation of which permits removal of the pin 26 from the outer plunger cutout 45. Additionally, a through-hole 28 introduced into the barrel 3 can be arranged on the side of the pin 26 facing away from the predetermined breaking point 27, which through-hole 28 makes it easier to remove the pin 26 from the outer plunger cutout 45. It is also conceivable that the locking device is designed such that the pin 26 is removed from the outer plunger cutout 45 by pressing the inner plunger 7. This can be achieved with the second inner plunger portion 30 pressing the pin 26 radially outward. For this purpose, the pin 26 can have a pin flank 26a, on which the end of the second inner plunger portion 30 facing toward the cannula 12 slides and in doing so presses the pin 26 radially outward.

Figure 5:
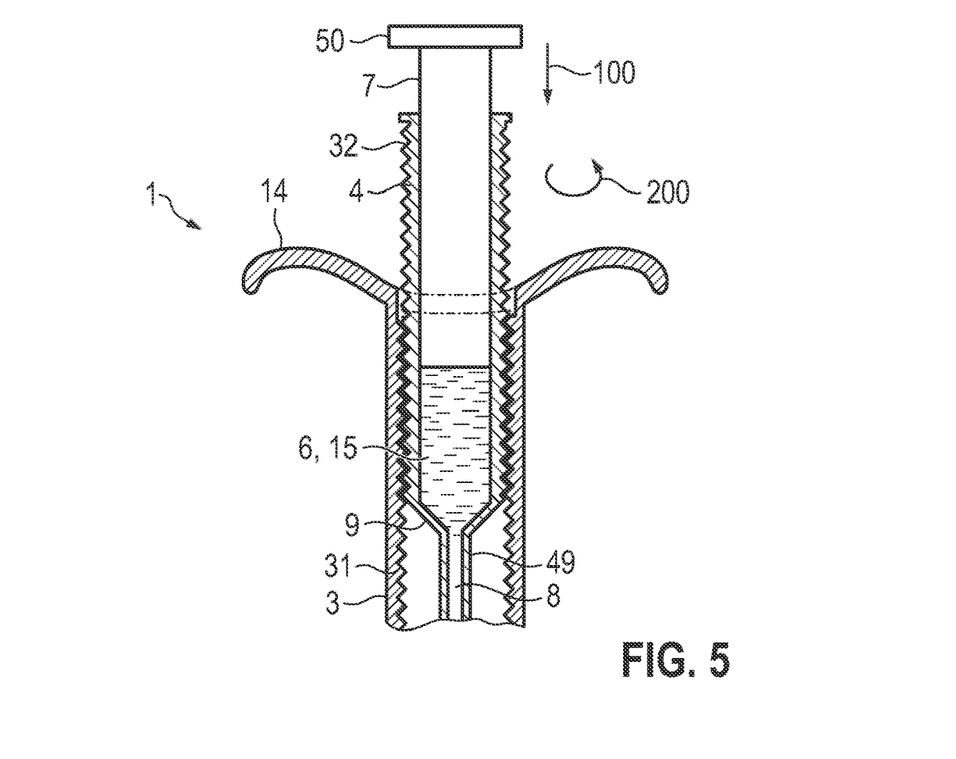
FIG. 5 shows a fourth exemplary embodiment of the injector.

As can be seen from FIG. 5, the injector 1 can be designed such that the first movement 100 is effected with a translation movement of the inner plunger 7, and the second movement 200 is effected with a screwing movement of the outer plunger 4. For this purpose, the barrel 3 can have an internal thread 31 and the outer plunger 4 can have an external thread 32, wherein the internal thread 31 and the external thread 32 are in engagement with each other.

FIG. 6 shows an exemplary embodiment in which the injector 1 is designed to receive a cartridge 33 in which the liquid 15 is arranged, as a result of which the liquid 15 can be introduced into the outer plunger cavity 6. The cartridge 33 has the seal 10 and a further seal 34, wherein the seal 10 and the further seal 34 delimit the liquid 15 at ends of the cartridge 33 that face away from each other. The further seal 34 is intended to be pierced through by the inner plunger 7. In its interior, the barrel 3 can have a stop 40 which is designed to support the cartridge 33 at its end facing toward the cannula 12.

As can be seen from FIG. 7, the injector 1 can have a heating element which is designed to heat the outer plunger cavity 6. The heating element can have a latent heat store, which is a supersaturated solution 36 which is arranged in a container 35 and which is designed to emit heat through crystallization of the supersaturated solution. As is shown in FIG. 7, the container 35 can be part of the inner plunger 7. FIG. 7 shows a portion of the injector 1 at two different time points, wherein the earlier time point is shown on the left, and the later time point is shown on the right. At the earlier time point, the container 35 is separate from the rest of the inner plunger 7, wherein the rest of the inner plunger 7 has, at its end facing toward the cannula 12, a crystallization protuberance 37 which is designed, during the first movement, to contact the supersaturated solution 36 and thereby trigger the crystallization. By movement of the rest of the inner plunger 7 in the direction toward the cannula 12, the crystallization protuberance 37 contacts the supersaturated solution 36, as a result of which a crystallized solution arises from the supersaturated solution 36 at the second time point. Thus, a heat transfer 38 takes place from the crystallized solution 39 into the liquid 15. At its end facing away from the cannula 12, the container 35 can have, for example, a foil 51 which holds the supersaturated solution 36 in the container 35 and which is designed to be pierced through by the crystallization protuberance 37. The crystallization protuberance 37 can be a seed crystal, for example.

Figure 8:
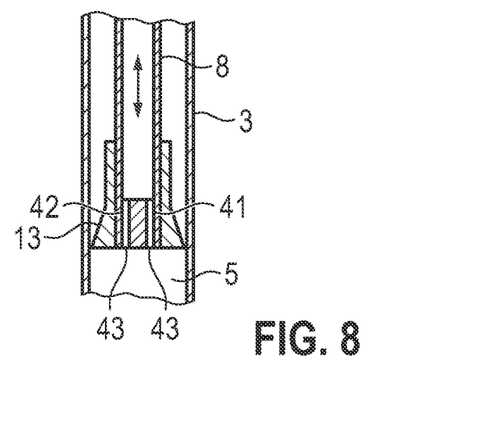
FIG. 8 shows a cushion of the injector according to an exemplary embodiment of the disclosure.

FIG. 8 shows that a rigid channel 41 is formed in the cushion 13, which rigid channel 41 is designed not to be deformed when it enters the narrowed part 11, and it thus allows the liquid 15 from the barrel cavity 5 to flow in a direction away from the cannula 12. Moreover, in addition to or instead of the rigid channel 41, the cushion 13 can have a flexible channel 42, which is designed to be deformed, when moved into the narrowed part 11, and thus makes it difficult for the liquid 15 to flow from the barrel cavity 5 in a direction away from the cannula 12. The amount of liquid 15 that emerges from the cannula 12 together with the intraocular lens 2 can be set via the rigid channel 41 and, optionally, the flexible channel 42.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS 1 ophthalmosurgical injector
2 intraocular lens
3 barrel
4 outer plunger
5 barrel cavity
6 outer plunger cavity
7 inner plunger
8 channel
9 nozzle
10 seal
11 narrowed part
12 cannula 13 cushion
14 handle
15 liquid
16 insertion direction
17 switching mechanism
18 projection
19 cutout
20 first region
21 second region
22 contact surface
22a switching mechanism projection
23 outer plunger projection
24 pretensioning means
25 further outer plunger cavity 26 pin
26a *pin flank*
27 predetermined breaking point
28 through-hole
29 first inner plunger portion
30 second inner plunger portion
31 internal thread
32 external thread
33 cartridge
34 further seal
35 container
36 supersaturated solution
37 crystallization protuberance
38 heat transfer
39 crystallized solution
40 stop
41 rigid channel
42 flexible channel
43 opening
44 first outer plunger wall portion
45 outer plunger cutout
46 second outer plunger wall portion
47 third outer plunger wall portion
48 spring support
49 channel wall
50 thickened part
51 foil
100 first movement
200 second movement

What is claimed is:

1. An ophthalmosurgical injector, comprising:
a cannula;
a barrel;
an outer plunger mounted in the barrel in a longitudinally displaceable manner and together with the barrel delimiting a barrel cavity arranged in the barrel, and into which an intraocular lens can be introduced; and
an inner plunger mounted in the outer plunger in the longitudinally displaceable manner and together with the outer plunger delimiting an outer plunger cavity arranged in the outer plunger, and into which a liquid can be introduced,
wherein the ophthalmosurgical injector is configured such that a first movement, executed by the inner plunger relative to the outer plunger such that the outer plunger cavity becomes smaller, causes the liquid to flow from the outer plunger cavity into the barrel cavity via an opening arranged in the outer plunger, and a second movement, executed by the outer plunger relative to the barrel such that the barrel cavity becomes smaller, causes the intraocular lens to be pressed out of the barrel cavity and into the cannula,
wherein the outer plunger has, at an end of the outer plunger delimiting the barrel cavity, a cushion which is configured to contact the intraocular lens during the second movement,
wherein the cushion is softer than other portions of the outer plunger,
wherein a rigid channel is formed in the cushion, and
wherein the rigid channel allows the liquid from the barrel cavity to flow in a direction away from the cannula.

2. The ophthalmosurgical injector as claimed in claim 1, wherein the outer plunger has a seal which seals off the outer plunger cavity from the barrel cavity and which is configured to be caused to burst with the first movement.

3. The ophthalmosurgical injector as claimed in claim 1, wherein the outer plunger has a nozzle via which the liquid flows from the outer plunger cavity into the barrel cavity.

4. The ophthalmosurgical injector as claimed in claim 1, wherein:
the barrel cavity has a narrowed part at an end of the barrel cavity facing away from the outer plunger, and
the cushion is configured such that the cushion, when moved into the narrowed part, is deformed such that the opening is reduced in size or closed.

5. The ophthalmosurgical injector as claimed in claim 1, wherein the outer plunger has a channel arranged directly upstream from the opening via which the liquid flows to the opening during the first movement, and a channel wall, which delimits the channel and which is arranged at a distance from the barrel.

6. The ophthalmosurgical injector as claimed in claim 1, wherein the ophthalmosurgical injector has a locking device which has a locked state, in which the second movement is blocked and the first movement is permitted, and an unlocked state, in which the second movement is no longer blocked.

7. The ophthalmosurgical injector as claimed in claim 6, wherein:
the locking device has a pin mounted on the barrel,
the outer plunger has a first outer plunger wall portion, in which an outer plunger cutout is formed,
in the locked state, the pin is arranged in the outer plunger cutout, and
in the unlocked state, the pin is arranged outside the outer plunger cutout.

8. The ophthalmosurgical injector as claimed in claim 7, wherein:
in the locked state, the pin is mounted fixedly on the barrel and protrudes inward from the barrel, and the barrel has a predetermined breaking point, and
deformation of the predetermined breaking point permits removal of the pin from the outer plunger cutout.

9. The ophthalmosurgical injector as claimed in claim 7, wherein the barrel has a barrel through-hole through which, in the locked state, the pin extends into the outer plunger cutout.

10. The ophthalmosurgical injector as claimed in claim 6, wherein:
the barrel has a cutout with a first region and a second region, and the locking device has a switching mechanism arranged in the barrel and which is configured to abut the outer plunger in order thereby to block the second movement, and has a projection which engages in the cutout, and
in the locked state, the projection engages in the first region, from where the projection can be brought into the second region by a rotation of the switching mechanism, as a result of which the locking device reaches the unlocked state.

11. The ophthalmosurgical injector as claimed in claim 10, wherein an end of the first region facing toward the cannula is arranged farther away from the cannula than an end of the second region facing toward the cannula.

12. The ophthalmosurgical injector as claimed in claim 10, wherein the ophthalmosurgical injector is configured to convert part of the second movement into the rotation of the switching mechanism.

13. The ophthalmosurgical injector as claimed in claim 1, wherein the ophthalmosurgical injector is configured such that the first movement is effected with a translation movement of the inner plunger, and the second movement is effected with a screwing movement of the outer plunger.

14. The ophthalmosurgical injector as claimed in claim 1, wherein the ophthalmosurgical injector has a heating element configured to heat the outer plunger cavity.

15. The ophthalmosurgical injector as claimed in claim 14, wherein the heating element has a latent heat store.

16. The ophthalmosurgical injector as claimed in claim 15, wherein the latent heat store is a supersaturated solution, which is configured to emit heat through crystallization of the supersaturated solution.

17. The ophthalmosurgical injector as claimed in claim 16, wherein the inner plunger has a crystallization protuberance which is configured, during the first movement, to contact the supersaturated solution and thereby trigger the crystallization.

18. The ophthalmosurgical injector as claimed in claim 1, wherein the ophthalmosurgical injector is configured to receive a cartridge in which the liquid is arranged, as a result of which the liquid can be introduced into the outer plunger cavity.

19. The ophthalmosurgical injector as claimed in claim 1, wherein the ophthalmosurgical injector has the liquid, and the liquid is arranged in the outer plunger cavity.

20. The ophthalmosurgical injector as claimed in claim 19, wherein the liquid has a lubricant and/or a physiological saline solution.

21. An ophthalmosurgical injector, comprising:

a cannula;

a barrel;

an outer plunger mounted in the barrel in a longitudinally displaceable manner and together with the barrel delimiting a barrel cavity arranged in the barrel, and into which an intraocular lens can be introduced; and an inner plunger mounted in the outer plunger in the longitudinally displaceable manner and together with the outer plunger delimiting an outer plunger cavity arranged in the outer plunger, and into which a liquid can be introduced, wherein the ophthalmosurgical injector is configured such that a first movement, executed by the inner plunger relative to the outer plunger such that the outer plunger cavity becomes smaller, causes the liquid to flow from the outer plunger cavity into the barrel cavity via an opening arranged in the outer plunger, and a second movement, executed by the outer plunger relative to the barrel such that the barrel cavity becomes smaller, causes the intraocular lens to be pressed out of the barrel cavity and into the cannula, wherein the outer plunger has, at an end of the outer plunger delimiting the barrel cavity, a cushion which is configured to contact the intraocular lens during the second movement, wherein the cushion is softer than other portions of the outer plunger, and wherein the ophthalmosurgical injector has the intraocular lens, and the intraocular lens is arranged in the barrel cavity.

* * * * *